United States Patent [19]

Schmidt et al.

[11] Patent Number: 4,824,886
[45] Date of Patent: Apr. 25, 1989

[54] 2-PHOSPHONO-BUTANE-1,2,4,-TRICARBOXYLIC ACID EMULSIFIER DERIVATIVES

[75] Inventors: Adolf Schmidt, Cologne; Udo Hendricks, Odenthal, both of Fed. Rep. of Germany

[73] Assignee: Bayer Aktiengesellschaft, Leverkusen-Bayerwerk, Fed. Rep. of Germany

[21] Appl. No.: 229,806

[22] Filed: Aug. 8, 1988

Related U.S. Application Data

[63] Continuation of Ser. No. 13,366, Feb. 11, 1987, abandoned.

[30] Foreign Application Priority Data

Feb. 22, 1986 [DE] Fed. Rep. of Germany ....... 3605800

[51] Int. Cl.$^4$ ............................ C08K F/53; C08F 2/28
[52] U.S. Cl. ................................... 524/131; 526/193; 526/340.1; 526/911
[58] Field of Search .............. 524/131; 526/193, 340.1

[56] References Cited

U.S. PATENT DOCUMENTS

| | | | |
|---|---|---|---|
| 3,886,204 | 5/1975 | Geffers et al. | 260/501.21 |
| 3,886,205 | 5/1975 | Geffers et al. | 558/180 |
| 4,267,278 | 5/1981 | Lindner et al. | 525/6 |

FOREIGN PATENT DOCUMENTS

| | | |
|---|---|---|
| 0019701 | 4/1980 | European Pat. Off. . |
| 0714708 | 2/1942 | Fed. Rep. of Germany ..... 39 A/14 |
| 59-29697 | 2/1984 | Japan . |

OTHER PUBLICATIONS

CA 101:111197t (1984).
Kunststoff-Handbuch, "Polyamide", Band VI, Carl Hanser Verlag, Munich, West Germany, 1966.
Derwent Japanese Patents Report, Derwent Publications, Ltd., 1987.
Chemical Abstracts, vol. 101, p. 681 (1984).

*Primary Examiner*—Veronica P. Hoke
*Attorney, Agent, or Firm*—Connolly & Hutz

[57] ABSTRACT

The invention relates to 2-phosphonobutane-1,2,4-tricarboxylic acid derivatives, which can be obtained by reaction of the tricarboxylic acid with $C_{6-20}$-alcohols and which are suitable as auxiliaries (emulsifiers) for emulsion polymerization.

3 Claims, No Drawings

2-PHOSPHONO-BUTANE-1,2,4,-TRICARBOXYLIC ACID EMULSIFIER DERIVATIVES

This application is a continuation of application Ser. No. 013,366, filed 2/11/87, now abandoned.

The invention relates to 2-phosphonobutane-1,2,4-tricarboxylic acid derivatives of the general formula (I), which can be obtained by reaction of the tricarboxylic acid (II) (2-phosphonobutane-1,2,4-tricarboxylic acid: "PBSAN") with $C_{6-20}$-alcohols optionally followed by neutralization and which are suitable as auxiliaries (emulsifiers) for emulsion polymerization.

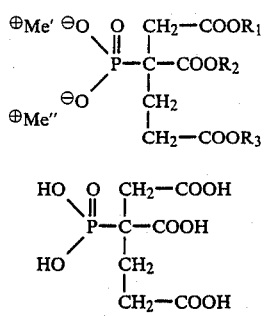

In formula (I), $^\oplus Me'$ and $^\oplus Me''$ denote a monovalent cation, particularly of potassium, sodium, lithium, ammonium or hydrogen. The radicals $R_1$ to $R_3$ denote independently $C_{6-20}$-alkyl or cycloalkyl radicals, and one or two of these radicals, independently of one another, can also be $^\oplus Me'$.

It is known from EP-A-4062 that aqueous dispersions of vinyl polymers can be prepared in the presence of an emulsifier and at least one salt of a phosphonic acid derivative containing at least two phosphorus atoms and acting as a dispersing agent. Polymer dispersions made in this way are suitable as coating agents and for impregnation, coating and adhesion of solid materials. However, to obtain stable polymer dispersions, the concomitant use of conventional emulsifiers is necessary.

German Offenlegungsschrift No. 2,723,834 discloses reaction products of phosphonocarboxylic acids with alcohols which are produced by mixing phosphonocarboxylic acids with mono- and/or polyhydric alcohols in the molar ratio from about 50:1 to 1:50. Suitable alcohol components are n-alkanols having up to 6 C atoms, cyclohexanol and alcohols with more than one OH group. These mixtures are used as agents for conditioning water and aqueous slurries. Such mixtures are not suitable as emulsifiers for emulsion polymerization.

Finally, European Patent Application No. 19,701 discloses that ABS moulding materials with improved surface properties can be prepared using phosphonocarboxylic acid derivatives of the formula (III),

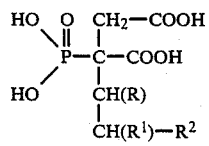

in which
R denotes hydrogen, $C_{1-4}$-alkyl or carboxyl,
$R^1$ denotes hydrogen or methyl, and
$R^2$ denotes carboxyl.

These compounds are not suitable as emulsifiers in emulsion polymerization, as they cause coagulation.

It is an object of this invention to provide derivatives of 2-phosphonobutane-1,2,4-tricarboxylic acid according to formula (I)

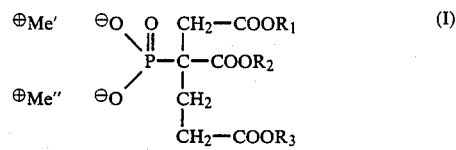

in which
$^\oplus Me'$ and $^\oplus Me''$, independently of one another, denote hydrogen, sodium, potassium, lithium or ammonium, and the radicals $R^1$ to $R^3$, independently of one another, denote alkyl radicals and/or cycloalkyl radicals having 6 to 20 C atoms, and one or two of these radicals $R^1$ to $R^3$ can also be $^\oplus Me$.

Another object is a process for the preparation of emulsifiers from derivatives of 2-phosphonobutane-1,2,4-tricarboxylic acids, wherein a mixture of 2-phosphonobutane-1,2,4-tricarboxylic acid and water is heated with $C_{6-20}$-alcohols in the molar ratio 1:1 to 1:4 for acid to alcohol, optionally in the presence of solvents functioning as entrainers, with separation and collection of water, and optionally with addition of additives which catalyse the esterification, and the still acidic reaction mixture, after removal of the solvent used as entrainer and of excess alcohol if any is dissolved or emulsified in water with addition of aqueous solutions which react in an alkaline manner.

Still another object is the application of the 2-phosphonobutane-1,2,4-tricarboxylic acid derivatives of formula I as emulsifiers in emulsion polymerization processes and as stabilizers for polymers against degradation by heat.

The 2-phosphonobutane-1,2,4-tricarboxylic acid derivatives can be produced for example as follows: Compounds of the formula (II) are esterified using $C_{6-20}$-alkanols and the water produced during the reaction is removed.

For this purpose, the compound (II) is reacted with 1 to 3 mol of a $C_{6-20}$-alkanol with elimination of water and removal of this water. This water of reaction can be removed either from the mixture or the melt of the starting products under reduced pressure or azeotropically with the aid of a suitable entrainer such as toluene.

Only the carboxyl groups are esterified during the esterification of the phosphonocarboxylic acid (II).

After the removal of the water of reaction and of the solvent used as entrainer, the residue is dissolved or emulsified in warm water, aqueous solutions of KOH, NaOH, $NH_3$ or organic compounds which react basically being added. During this, the pH should be between 5 and 10, preferably between 6 and 8. Preferred bases are potassium hydroxide and/or sodium hydroxide.

The emulsifier properties of component of formula I with respect to their capability of producing fine or coarse latices can be changed by varying the molar input ratio of phosphonobutanetricarboxylic acid to alkanol and also by the molecular weight of the alkanol.

Products of the reaction of 1 mol of 2-phosphonobutane-1,2,4-tricarboxylic acid with 1 mol of a $C_{10-20}$-alkanol are produced in one embodiment of the invention. When employed as emulsifiers they yield polymer latices having particle diameters <100 nm. These reaction products correspond to formula I when only one of the radicals $R_1$-$R_3$ is an alkyl radical (of course the reaction product is a mixture of different compounds). If 1 mol of 2-phosphonobutane-1,2,4-tricarboxylic acid is reacted with 2 mols of a $C_{8-20}$-alkanol in another embodiment the reaction product is an emulsifier which permits the preparation of polymer latices having particle diameters of about 100 to 350 nm. This reaction product corresponds to formula I where two of the radicals $R_1$-$R_3$ are alkyl (again mixtures of different compound are obtained).

Finally, if 1 mol of the tricarboxylic acid (II) is reacted with 3 mol of $C_{6-20}$-alkanol, the resulting reaction product is only sparingly water-soluble even in the salt form, but becomes soluble in monomers, particularly in the case of greater chain length. Thus, it permits the preparation of coarse polymer latices having particle diameters <200 nm, especially when the alcohol radicals are very long or bulky. These reaction products also correspond to formula I, but all radicals $R_1$-$R_3$ are now alkyl.

Suitable alcohols are $C_{6-20}$-n-alkanols, branched $C_{6-20}$-alkanols, such as 2-ethylhexanol, and/or cyclic $C_{6-20}$-alkanols, such as cyclohexanol or dehydroabietyl alcohol. Examples are n-hexanol, n-octanol, n-decanol, n-dodecanol, stearyl alcohol, n-octahexanol.

The polymers prepared with the aid of the emulsifiers of the formula (I) only display a slight tendency toward browning on heating, particularly in the case of polymers, such as polybutadiene, which are themselves sensitive in this respect.

If the neutralized or acidic products of the reaction between one mol of alcohol and 1 mol of 2-phosphonobutane-1,2,4-tricarboxylic acid are added to latices, for example to a polybutadiene latex, then films prepared from this latex display considerably less yellowing on heating than do films from the untreated latex. In particular, the crude colour quality of polybutadiene latex films from such latices which have been prepared using conventional emulsifiers of the 2-phosphonobutane-1,2,4-tricarboxylic acid type.

The emulsifiers according to the invention are distinguished, in addition, by low volatility and a little tendency toward turbidity of polymers.

Latices prepared using conventional emulsifiers can be coagulated using acidic esters of 2-phosphonobutane-1,2,4-tricarboxylic acid. The properties of such coagulates are improved with respect to the colour stability on heating compared to those obtained by conventional methods of coagulation.

With the aid of the emulsifiers according to the invention, monomers such as butadiene, ethylene, chloroprene, vinyl chloride, isoprene, vinyl bromide, vinyl fluoride, styrene, p-chlorostyrene, p-methylstyrene, acrylates such as methyl acrylate, ethyl acrylate, n-butyl acrylate and 2-ethylhexyl acrylate, methacrylates such as methyl methacrylate and n-butyl methacrylate, and vinyl esters such as vinyl acetate, vinyl propionate and vinyl versate can be polymerized or copolymerized. α-Methylstyrene, acrylonitrile and methacrylonitrile may be mentioned as further monomers which can be copolymerized with the monomers mentioned.

Homopolymers of butadiene and copolymers of butadiene with styrene and/or acrylonitrile or acryl esters such as n-butyl acrylate are particularly preferred. Furthermore copolymers of styrene with n-butyl acrylate.

The mechanical stability of the dispersions can be improved or properties such as adhesion, rheology and the ability to crosslink can be modified by concomitant use, besides of the main monomers mentioned, of comonomers carrying further hydrophilic groups, such as acrylic acid, methacrylic acid, acrylamide, methacrylamide, monoesters of maleic acid and monoesters of fumaric acid, or comonomers containing crosslinking groups, such as, for example, n-methylolmethacrylamide or its methyl ether. Likewise, crosslinking agents of the bisacrylate type or triallyl cyanurate can be employed. Latices for paints, paper coating materials, and binders for textile printing, coating the backs of carpets and the finishing of leather can be prepared in this fashion. The particularly preferred area of application of the emulsifiers according to the invention is in the preparation of rubber latices which serve as the base for the preparation of graft products. The emulsifiers according to the invention are also advantageously employed in the subsequent graft polymerization.

The polymerization reactions using the emulsifiers according to the invention can be initiated by the conventional free-radical generators, such as are described, for example, in: Houben-Weyl, Volume XIV/1, page 209–297 (G. Thieme Verlag, Stuttgart, 1961), in the temperature range from +5 to +95° C. The initiators can be water-soluble or alternatively monomer-soluble.

The concentrations specified in the examples below are always % by weight, unless otherwise stated.

EXAMPLE 1

Preparation of an emulsifier from 1 mol of PBSAN with 1 mol of stearyl alcohol 270 parts by weight of 2-phosphonobutane-1,2,4-tricarboxylic acid, 270 parts by weight of demineralized water, 270 parts by weight of stearyl alcohol and 800 parts by weight of toluene are mixed and heated to reflux on a water separator. When the separation of the water is complete, the toluene is removed by distillation in vacuo and the residue, before cooling, stirred with dilute sodium hydroxide solution, the pH being adjusted to 9.5 and the solids content being adjusted to 10%. This 10% strength solution is used as emulsifier.

Polymerization

The following are poured into a stainless steel autoclave equipped with external jacket temperature control and electronic regulation of the internal temperature, adjustable stirrer, and pressure, temperature and pH measuring means, oxygen being excluded:
demineralized water—2023.0 parts by weight,
10% strength emulsifier solution—547.0 parts by weight,
tert.-dodecylmercaptan—5.7 parts by weight,
butadiene—1832.0 parts by weight.

The mixture is heated to 65° C. while stirring with a paddle stirrer (120 min$^{-1}$), after which 175 parts by weight of a 2.5% strength potassium persulphate solution are added.

After 15 hours, a latex having a solids content of 40% and an average latex particle diameter of 70 nm (DAV, see DIN 53206) is produced. The latex does not foam during the subsequent degassing in vacuo. It has a viscosity of 25 centipoise (measured in a Brookfield viscosimeter, spindle 1 at 6–60 rpm, 25° C. and a solids content of 40%).

Films which are drawn from this latex and which are adjusted to a wet film thickness of 90 μm with the aid of a coating applicator, dried initially at room temperature and are subsequently stored at 150° C. for 120 minutes are still virtually colourless after this time.

The latex thus prepared is subjected, after adjustment of the pH to 9.0, to pressure agglomeration by methods known per se with the aid of a homogenizer of the Manton Gaulin type at 20° C. and 400 bar to form an agglomerate having an average particle diameter of 250 nm (DAV). These pressure agglomerates can be used as graft bases for the preparation of ABS or other thermoplastic moulding materials.

EXAMPLE 2

Preparation of an emulsifier from 1 mol of PBSAN with 2 mol of n-octanol

A mixture of 160 parts by weight of PBSAN, 160 parts by weight of demineralized water, 300 parts by weight of toluene and 156 parts by weight of n-octanol is heaed to boiling on a water separator until the distillate passing over is dry and clear. The toluene is subsequently removed in vacuo and the viscous, brownish oil remaining (285 parts by weight) is stirred, simultaneously with 20% strength potassium hydroxide solution, into 750 parts by weight of demineralized water at 50° C., the addition of base being controlled in such a manner that the solution always reacts neutrally. The mixture is subsequently cooled to 20° C. and the pH of the cooled solution adjusted to 8.5. The solids content of the emulsifier solution thus obtained is adjusted to 15%.

Polymerization

The following are poured into an autoclave (analogously to Example 1):
demineralized water—4130.0 parts by weight,
sodium bicarbonate—9.2 parts by weight,
15% strength emulsifier solution—500.0 parts by weight,
tert.-dodecylmercaptan—13.1 parts by weight,
butadiene—3280.0 parts by weight.

As described in Example 1, the mixture is heated to 65° C. and 350 parts by weight of 2.5% strength potassium peroxodisulphate solution are subsequently added.

After 20 hours, a bluish shimmering latex having a solids content of 40% is obtained which is free of coagulate or specks. The average latex particle diameter is: 86 nm (DAN), 101 nm (DAF), 110 nm (DAV), determined by ultracentrifuge measurement.

EXAMPLE 3

Preparation of an emulsifier from 1 mol of PBSAN and 2 mol of n-dodecanol

A mixture of 122 parts by weight of PBSAN, 122 parts by weight of demineralized water. 171 parts by weight of n-dodecanol and 300 parts by weight of toluene are heated to boiling on a water separator until a clear distillate passes over, and the mixture is subsequently concentrated in vacuo. The residue is stirred, with simultaneous addition of 20% strength potassium hydroxide solution, into warm water, the addition of base being controlled in such a manner that the mixture reacts neutrally. After cooling, the pH is adjusted to 8.5 and the solids content of the emulsion produced is adjusted to 15%.

Polymerization

The batch of Example 2 is repeated using this emulsifier solution, the following relationship between the solids content of the latex obtained and the polymerization time being established:

| Polymerization time [h] | Solids content [%] |
| --- | --- |
| 5 | 10 |
| 10 | 29 |
| 15 | 38 |
| 20 | 40 |

The coagulate-free, bluish shimmering latex does not contain any specks. The latex particle diameter is:
80 nm (DAN), 91 nm (DAF), 98 nm (DAV),
determined by ultracentrifuge measurement.

EXAMPLE 4

Preparation of an emulsifier from 1 mol of PBSAN and 3 mol of n-octanol

A mixture of 117 parts by weight of PBSAN, 117 parts by weight of demineralized water and 170 parts by weight of n-octanol are heated on a water separator analogously to Example 2 until water no longer passes over. The brownish oil remaining after the removal of the toluene (226 parts by weight) is added dropwise, with simultaneous addition of 20% strength potassium hydroxide solution, to warm water in such a fashion that the mixture reacts neutrally. The pH is subsequently adjusted to 8. The solids content of the resulting emulsion is adjusted to 15%.

Polymerization

The following are transferred to an autoclave as described in Example 2:
demineralized water—2056.0 parts by weight,
sodium bicarbonate—4.6 parts by weight,
tert.-dodecyl mercaptan—6.6 parts by weight,
15% strength emulsifier solution—250.0 parts by weight,
butadiene—1640.0 parts by weight.

After heating to 65° C., 200 parts by weight of a 2.5% strength potassium persulphate solution are added. The following relationship is found between the polymerization time and the solids content of the latex:

| Polymerization time [h] | Solids content [%] |
| --- | --- |
| 5 | 8 |
| 10 | 14 |
| 15 | 21.5 |
| 20 | 28.5 |
| 25 | 33 |
| 30 | 38 |
| 40 | 40. |

The coagulate-free latex appears green in reflected light and red in transmitted light. The latex particle diameter is:
160 nm (DAN), 174 nm (DAF), 181 nm (DAV),
determined by ultracentrifuge measurement.

EXAMPLE 5

Preparation of an emulsifier from 1 mol of PBSAN and 3 mol of n-hexanol

A mixture of 135 parts by weight of PBSAN, 135 parts by weight of demineralized water, 153 parts by weight of n-hexanol, 400 parts by weight of toluene and 0.5 part by weight of p-toluenesulphonic acid is heated to boiling on a water separator until a dry distillate passes over. The clear solution is concentrated and the solvent-free residue (240 parts by weight of a brown oil) is added dropwise, simultaneously with 20% strength potassium hydroxide solution, to 500 parts by weight of water at 70° C. in such a manner that a pH of 8 is maintained.

The solids content of the emulsion is subsequently adjusted to 15% by addition of water.

Polymerization

The following are transferred to an autoclave analogously to Example 1:
demineralized water—2086.0 parts by weight,
sodium bicarbonate—4.6 parts by weight,
tert.-dodecyl mercaptan—6.6 parts by weight,
15% strength emulsifier solution—272.0 parts by weight,
butadiene—1640.0 parts by weight.

After heating to 65° C., 200 parts by weight of a 2.5% strength potassium peroxodisulphate solution are added.

After 40 hours, a solids content of 37% is achieved. The average diameter of the latex particles is:
171 nm (DAN), 195 nm (DAF), 204 nm (DAV), determined by ultracentrifuge measurement.

EXAMPLE 6

Preparation of an emulsifier from 1 mol of PBSAN and 3 mol of n-dodecanol

A mixture of 135 parts by weight of PBSAN, 135 parts by weight of demineralized water, 279 parts by weight of n-dodecanol, 1 part by weight of p-toluenesulphonic acid and 400 parts by weight of toluene are heated to boiling on a water separator until a clear distillate passes over, and subsequently concentrated in vacuo. The residue, 360 parts by weight of a yellow oil, is heated to 100° C. and stirred into 750 parts by weight of water having a temperature of 60° C., the pH of the mixture being adjusted to 6 by the simultaneous addition of 20% strength potassium hydroxide solution. After cooling to 25° C., the pH is adjusted to 8.5 and the solids content of the emulsion to 15% by weight.

Polymerization

The following are placed in an autoclave analogously to Example 1:
demineralized water—2071.0 parts by weight,
sodium bicarbonate—4.6 parts by weight,
tert.-dodecyl mercaptan—6.6 parts by weight,
15% strength emulsifier solution—272.0 parts by weight,
butadiene—1640.0 parts by weight.

After heating to 65° C., 200 parts by weight of a 2.5% strength potassium peroxodisulphate solution are added.

After 30 hours, a solids content of the latex of 38% is achieved. The average diameter of the latex particles is:
129 nm (DAN), 145 nm (DAF), 160 nm (DAV), determined by ultracentrifuge measurement.

EXAMPLE 7

Preparation of an emulsifier from 1 mol of PBSAN and 2 mol of n-octadecanol

A mixture of 102 parts by weight of PBSAN, 101 parts by weight of demineralized water, 204 parts by weight of n-octadecanol, 400 parts by weight of toluene and 1 part by weight of p-toluenesulphonic acid were heated to boiling on a water separator until a clear distillate passed over, and subsequently concentrated in vacuo. The brownish oil which remains is added dropwise while still hot (100° C.) into 750 parts by weight of water having a temperature of 60° C., the pH of the mixture being held at 6-7 by addition of 20% strength potassium hydroxide solution. After cooling to 25° C., the pH is adjusted to 8.5 and the solids content of the emulsion to 15%.

Polymerization

The following are transferred an autoclave analogously to Example 1:
demineralized water—4120.0 parts by weight,
sodium bicarbonate—9.2 parts by weight,
tert.-dodecyl mercaptan—13.2 parts by weight,
15% strength emulsifier solution—544.0 parts by weight,
butadiene—3280.0 parts by weight.

After heating to 65° C., 400 parts by weight of a 2.5% strength potassium peroxodisulphate solution are added.

After 55 hours, a solids content of the latex of 38% is achieved. The average diameter of the latex particles is:
175 nm (DAN), 219 nm (DAF), 240 nm (DAV), determined by ultracentrifuge measurement.

EXAMPLE 8

The polymerization of styrene is carried out using the emulsifiers below:
Emulsifier I: Emulsifier according to Example 2,
Emulsifier II: Emulsifier according to Example 3,
Emulsifier III: Emulsifier according to Example 4.

The following emulsifier concentrations, relative to the monomer, were employed:
Experimental series A: 0.3% by weight,
Experimental series B: 0.7% by weight,
Experimental series C: 1.5% by weight,
Experimental series D: 3.0% by weight,
Experimental series E: 5.0% by weight,
(The % by weight data relate to styrene).

Relative to styrene, 0.3% by weight of potassium peroxodisulphate and 0.2% by weight of sodium bicarbonate were employed in all experiments. The polymerization was carried out at 65° C. for 10 hours. The (monomer):(monomer+water) ratio was 0.3 in all experiments.

The polymerization experiments were carried out in test tubes in a temperature-controlled laboratory apparatus (vortex vibrator).

Solids contents and average particle diameters of the latices obtained are collated in Table 1.

The average latex particle diameter decreases with increasing amount of emulsifier when the emulsifiers I and II are used.

A lesser decrease in the average particle diameter can be detected when emulsifer III is used. The solids content of the latices can be well below the maximum value of 30% by weight at very low amounts of emulsifier (0.3% by weight). The emulsifier III obtained by reaction of 1 mol of PBSAN with 3 mol of n-octanol permits the preparation of coarse, virtually monodisperse latices the particle diameters of which only vary slightly with the emulsifier concentration.

TABLE 1

| Example 8 Experimental Series | Emulsifier I SC | D | Emulsifier II SC | D | Emulsifier III SC | D |
|---|---|---|---|---|---|---|
| A | 17 | 219 | 20 | 190 | 15 | 230 |
| B | 29 | 196 | 28 | 160 | 28 | 263 |
| C | 29 | 142 | 30 | 143 | 28 | 243 |
| D | 30 | 113 | 30 | 126 | 29 | 197 |
| E | 30 | 112 | 29 | 114 | 30 | 198 |

SC: Solids content [% by weight]
D: Average particle diameter [nm] (DAV)

EXAMPLE 9

A mixture of:
demineralized water—121.5 parts by weight,
n-butyl acrylate—107.0 parts by weight, emulsifier according to Example 3, (5% strength aqueous solution)—65.0 parts by weight, 1% strength aqueous potassium peroxodisulphate solution—32.0 parts by weight.
is polymerized for 7 hours at 70° C. with stirring, oxygen being excluded. A coagulate-free latex having an average particle diameter of 100 nm is produced. The latex dries to form clear colourless films which do not discolour after 60 minutes at 150° C. in a drying cabinet.

EXAMPLE 10

Experiment 9 is repeated using ethyl acrylate in place of n-butyl acrylate. The latex is coagulate-free and the quality of the clear film from films dried from this latex corresponds to that of Example 9.

EXAMPLE 11

(comparison example)

A polybutadiene latex having an average particle diameter of 80 nm, prepared by emulsion polymerization of butadiene with the aid of 2% by weight of potassium oleate as emulsifier and 0.23% by weight of potassium peroxodisulphate, relative to the monomer, and a [(monomer):(monomer+water)] ratio of 0.4 is coated, with a wet film thickness of 90 μm, onto degreased and preheated glass plates with the aid of a coating applicator; and dried at room temperature until the film is clear. The film is subsequently dried for 2 hours at 150° C.

After this time, a clear yellowing of the films is observed, corresponding to the Hazen colour scale (DIN 53409) of about 40 to 60.

EXAMPLE 12

If the emulsifier prepared in Example 1 is added to the latex according to Example 11 in an amount of 1.5% by weight, relative to the polymer, then the discoloration improves to a value on the Hazen colour scale of 10 to 15 under the experimental conditions described in Example 11.

EXAMPLE 13

A polybutadiene latex which has been prepared in batches according to Example 11 with the aid of potassium oleate, and another polybutadiene latex which has been prepared in batches analogously to Example 11 with the aid of 2% by weight of a commercial emulsifier based on the Na salt of dehydroabietic acid (cf. Houben-Weyl, Vol. XIV/1, 1961, pages 195–196) and with 0.23% by weight of potassium peroxodisulphate are compared below with the latices prepared according to the invention in respect of their clear film properties.

For this comparison, the solids content of the latices is adjusted to 40% by weight after demonomerization. Films with a wet film thickness of 90 μm are subsequently drawn on hot glass plates, dried on at 22° C. and subsequently heated at 150° for 60 minutes. The discoloration of the latex films is assessed according to the HAZEN colour scale (DIN 53 409) with the aid of coloured plates supplied by HELLIGE GmbH (Freiburg i. Br.) the colour tone of which is compared with that of the films.

As can be seen from Table 1 below, the films from the latices prepared using emulsifiers according to the invention only have a slight tendency towards yellowing.

TABLE 1

| Serial No. | Corresponding Example | Polybutadiene latex, prepared using an emulsifier from: 1 mol of PBSAN and: | Discoloration of the films after drying in air at 150° C./1 h [HAZEN colour scale] | Average latex particle diameter [nm] (DAV) |
|---|---|---|---|---|
| 1 | 5 | 3 mol of n-hexanol | 5 | 204 |
| 2 | 2 | 2 mol of n-octanol | 10 | 110 |
| 3 | 4 | 3 mol of n-octanol | 5–10 | 181 |
| 4 | 3 | 2 mol of n-dodecanol | 10 | 98 |
| 5 | 6 | 3 mol of n-dodecanol | 15 | 160 |
| 6 | 1 | 1 mol of n-octadecanol | 0–5 | 70 |
| 7 | 7 | 2 mol of n-octadecanol | 10 | 240 |
| 8* | 11 | potassium oleate | 30–40 | 80 |
| 9* | 13 | Dresin acid, sodium salt (DRESINATE 731) | 15–25 | 100 |

*Comparison Example

We claim:
1. A method for stabilizing polymers against thermal degradation which comprises adding an efficient amount of a compound of formula I:

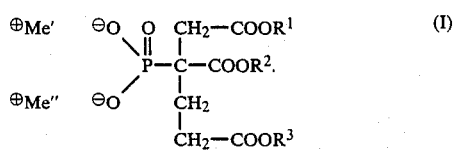

where
⊕Me' and ⊕Me", independently of one another, denote hydrogen, sodium potassium, lithium or ammonium, and the radicals $R^1$, $R^2$ and $R^3$, independently of one another, denote an alkyl containing 6 to 20 carbon atoms, a cycloalkyl radical containing 6 to 20 carbon atoms, or $\oplus Me'$, with the proviso that a maximum of two of the radicals $R^1$, $R^2$ and $R^3$ may simultaneously be $\oplus Me'$.

2. In an improved aqueous dispersion for the emulsion polymerization of ethylenically unsaturated monomers, the improvement which comprises the aqueous dispersion contains an emulsifier which is a derivative of 2-phosphonobutane-1,2,4-tricarboxylic acid according to formula (I)

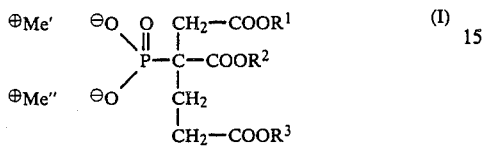

where
$\oplus Me'$ and $\oplus Me''$, independently of one another, denote hydrogen, sodium, potassium, lithium or ammonium, and the radicals $R^1$, $R^2$ and $R^3$, independently of one another, denote an alkyl containing 6 to 20 carbon atoms, a cycloalkyl radical containing 6 to 20 carbon atoms, or $\oplus Me'$, with the proviso that a maximum of two of the radicals $R^1$, $R_2$ and $R^3$ may simultaneously be $\oplus Me'$.

3. In an improved method for the emulsion polymerization of ethylenically unsaturated monomers in an aqueous dispersion, the improvement which comprises the aqueous dispersion contains an emulsifier which is a derivative of 2-phosphonobutane-1,2,4-tricarboxylic acid according to formula (I)

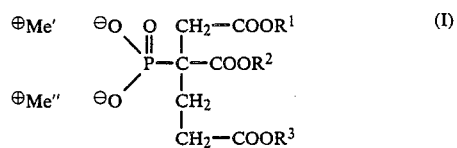

where
$\oplus Me'$ and $\oplus Me''$, independently of one another, denote hydrogen, sodium, potassium, lithium or ammonium, and the radicals $R^1$, $R^2$ and $R^3$, independently of one another, denote an alkyl containing 6 to 20 carbon atoms, a cycloalkyl radical containing 6 to 20 carbon atoms, or $\oplus Me'$, with the proviso that a maximum of two of the radicals $R^1$, $R^2$ and $R^3$ may simultaneously be $\oplus Me'$.

* * * * *